United States Patent
James

(10) Patent No.: US 6,784,144 B2
(45) Date of Patent: Aug. 31, 2004

(54) STABLE EMULSIONS

(75) Inventor: David James, Thornleigh (AU)

(73) Assignee: Dow Corning Australia Pty. Ltd., Pennant Hills (AU)

(*) Notice: Subject to any disclaimer, the term of this patent is extended or adjusted under 35 U.S.C. 154(b) by 0 days.

(21) Appl. No.: 10/068,365

(22) Filed: Feb. 5, 2002

(65) Prior Publication Data

US 2002/0119897 A1 Aug. 29, 2002

Related U.S. Application Data

(63) Continuation of application No. 09/581,578, filed as application No. PCT/AU98/01043 on Dec. 18, 1998, now Pat. No. 6,358,898.

(30) Foreign Application Priority Data

Dec. 22, 1997 (AU) .............................................. PP1081

(51) Int. Cl.$^7$ ................................................. A61K 7/00
(52) U.S. Cl. ...................... 510/130; 510/159; 510/417; 510/458; 510/481; 510/466
(58) Field of Search ................................. 510/130, 159, 510/417, 458, 481, 466, 460, 488, 491

(56) References Cited

U.S. PATENT DOCUMENTS

| | | | |
|---|---|---|---|
| 4,212,759 A | 7/1980 | Young et al. | 252/119 |
| 5,523,081 A | 6/1996 | Edwards et al. | 424/73 |
| 5,585,104 A | 12/1996 | Ha et al. | 424/401 |
| 5,650,384 A | 7/1997 | Gordon et al. | 510/159 |

FOREIGN PATENT DOCUMENTS

| | | |
|---|---|---|
| EP | 0 111 895 | 12/1983 |
| EP | 0 709 451 | 5/1996 |
| JP | 230953 | 7/1984 |
| JP | 59117589 | 7/1984 |
| JP | 3081400 | 4/1991 |

*Primary Examiner*—Necholus Ogden
(74) *Attorney, Agent, or Firm*—Duane Morris, LLP

(57) ABSTRACT

The invention describes a silicone oil emulsion stabilized with soap. The soap is formed in situ from one or more fatty acids and a cation of a base during the emulsification process.

The invention also provides a method of forming a soap stabilized oil-in-water emulsion including the steps of forming a first mixture comprising a silicone oil, a base, and initial water, combining the first mixture with a fatty acid component and emulsifying the resultant combination.

7 Claims, No Drawings

STABLE EMULSIONS

This application is a continuation of U.S. patent application Ser. No. 09/581,578, filed Jul. 25, 2000 now U.S. Pat. No. 6,358,898 which is a 371 of PCT/AU98/01043 filed Dec. 18, 1998, the disclosure of which is hereby incorporated herein by reference in its entirety.

FIELD OF THE INVENTION

The invention relates to soap stabilized emulsions and to the methods of manufacture of such emulsions, and in particular to silicone emulsions useful in personal care products.

BACKGROUND OF THE INVENTION

Traditionally, soap in the form of bars or flakes has been used as the preferred cleaning agent in personal care. In recent years, personal cleaning agents in the form of gels have become increasingly popular. These gels are sometimes referred to as shower gels. Such shower gels are extremely popular with consumers.

These shower gels commonly contain:
Detergents or surfactants which can be synthetic or natural soap.
Humectants such as glycerine and propylene glycol.
Chelating agents such as EDTA.
Buffers such as citrate or citric acid.
Pearlisers such as EGMS and mica.
Perfumes and Colours.
Thickeners such as hydroxy ethyl cellulose.
Water.

It is believed that the addition of silicones (commonly polydimethylsiloxane) to these gel formulations adds beneficiary sensory effects to the skin which may be observed during or after the use of the gel.

The proportions of each ingredient are selected to provide good cleaning ability and also to result in a product with a texture pleasant to the consumer. Shower gels can be classified according to the type of surfactants present e.g. all-synthetic surfactant, a blend of soap with synthetic surfactant and all natural soap with no synthetic surfactant.

A "Soap" as herein defined is composed of one or more carboxylates of long chain fatty acids in combination with one or more cations.

Consumer tests in markets where shower gels are most popular have shown that consumers can detect the difference between a shower gel containing synthetic surfactants and one containing all natural soap, and clearly prefer the 100% soap based gel.

All-synthetic surfactant based products are generally more stable and more easily prepared than soap based products. A number of silicone based compounds give suitably stable emulsions in conjunction with these all-synthetic surfactant products. While these emulsions are relatively easy to manufacture, and have good stability, they suffer from the drawback that consumers can detect a reduction in agreeable skin-feel of the product when compared with a 100% soap based gel. All-synthetic surfactant based products are also less attractive from a marketing point of view as they are not perceived by consumers as having the desirable property of being derived from natural sources. Shower gels containing a 100% soap (that is to say substantially exclusively soap as the surfactant), typically contain around 25% soap in total. As mentioned above, 100% soap based gels are preferable from a marketing point of view, because of their good skin-feel properties and their being perceived as more "natural" than synthetic surfactant based gels.

When manufacturing 100% soap based gels, the key raw materials are the long chain fatty acids which form the soaps. These tend to be a low melting solids or waxes which are difficult to process. Heating may be required when preparing the soap.

An even greater problem of the 100% soap based shower gels comprised of a silicone oil-in water emulsion is that such a combination of the soap based shower gel and the silicone oil is not stable. Currently no stable silicone emulsion with a 100% soap is known. Typically, the product begins to separate and exhibit distinct layers ie. a clear, lower water layer and an opaque layer containing components which are not water soluble or water miscible. This can happen quite rapidly, in some cases overnight. Such separated products are generally unacceptable to consumers.

Some silicone compounds provide limited stability for emulsions based on a blend of soaps and synthetic surfactants, with typically more than 5% synthetic surfactant being required. Shower gels which contain a synthetic surfactant/soap blend typically contain around 5 to 15% soap therein. Two types of synthetic surfactant can be used in combination with the soap, namely amphoteric surfactants (for example betaines) or non-ionic surfactants: (for example CDEA (coconut diethanolamines)). These surfactants are generally added at a level of 5% into the synthetic/soap surfactant blend. Generally silicone oil-in-water emulsions prepared using synthetic surfactants are stable in synthetic surfactant and soap/synthetic surfactant blend (generally provided that the synthetic surfactant level in the blend is greater than or equal to 5%) based shower gels, but such emulsions are not stable in soap surfactant shower gels.

The present invention seeks to overcome at least some of the disadvantages of the prior art or at least provide a commercial alternative thereto.

DESCRIPTION OF THE INVENTION

According to a first aspect the present invention consists in a silicone oil emulsion stabilized with soap, wherein the soap includes:
  one or more carboxylates of a fatty acid having from 8 to 18 carbon atoms; and
  a cation of a base, the soap being formed in situ from the fatty acid and the base during formation of the emulsion.

Preferably, the one or more carboxylates is a mixture having a similar distribution to that found in vegetable oils. More preferably, the distribution is that found in coconut oil or palm kernel oil. Most preferably, the mixture is derived from coconut oil. Table I shows typical compositions of Coconut and Palm oil which are suitable for use in the present invention.

It will be appreciated by those skilled in the art that compositions of coconut and palm kernel oil vary somewhat depending on the geographical origin, soil composition etc. The average compositions are summarised for the purposes of information only in the Table. The average compositions must be understood such that they may contain other fatty acids which have more or less carbon atoms than those described in the table. The compositions described in the table do not show any particular oil available from a single supplier, but rather give representative compositions. If it is desired to know the exact composition of the oil, this must be examined prior to production of the silicone emulsion.

These oils are available commercially, or may be obtained as precursors which may be converted into the desired fatty acids by chemical treatment such as hardening, cracking, saponification etc depending on the necessity thereof.

TABLE I

Composition of Coconut Oil and Palm Kernel Oil (% by weight)

| | Coconut Oil | Palm Kernel Oil |
|---|---|---|
| Caprylic Acid (C 8) | less than 10 | 1–7 |
| Capric Acid (C 10) | less than 10 | 1–10 |
| Lauric Acid (C 12) | 40–60 | 40–60 |
| Myristic Acid (C14) | 10–25 | 10–20 |
| Palmitic Acid (C16) | 5–15 | 5–15 |
| Stearic Acid (C18) | 1–20 | 1–5 |
| Oleic Acid (C18:1) | less than 10 | 5–20 |

The base is one which may be reacted with the above fatty acids to form a soap.

Preferably, the base is a trialkanolamine species, most preferably [$HN(CH_3CH_2OH)_3$]. However, mineral caustics, such as sodium hydroxide and potassium hydroxide may also be used.

Preferably the silicone oil is a "silicone fluid", and more preferably a polydiorganosiloxane. Such a polydiorganosiloxane is a linear polymer where the organo radical may be hydrogen, an alkyl group such as methyl, ethyl, propyl, butyl, an aryl group such as phenyl, an alkenyl group such as vinyl and the like. Preferably, the polymer terminates with —$Si(CH_3)_3$ ("trimethyl endcapped") or —$Si(CH_3)_2OH$ ("hydroxy endcapped") moieties. Preferably, the silicone oil used has a viscosity below 1,000,000 cps and more preferably below 100,000 cps. The oil may contain other functional groups, such as carboxy, halo etc. or any combination thereof.

The silicone oils of this invention are well known to those skilled in the art, with the most highly preferred compound being trimethylsilyl terminated polymethylsiloxane having the viscosity range described above.

As discussed below, the mean particle size of the emulsion is critical to provide a stable emulsion for use in a 100% soap based shower gel. Preferably the emulsion of the present invention is a "submicro-emulsion" with a mean particle size of less than 1.0 micrometers. More preferably the mean particle size is less than 1.0 micrometers and most preferably it is between 0.25 and 0.4 micrometers. Preferably at least d(90%) of the particles in the emulsion are less than 0.6 micrometers in size.

The present applicants have found that although the use of a single long chain fatty acid has been able to provide a stable silicone emulsion, these have not been suitable in shower gels. A blend of long chain fatty acids, wherein the carbon backbone varies from $C_8$ to $C_{18}$ has been found to produce a more stable emulsion.

Further, it has also been found that a significant and hitherto unexpected difference in the stability of the emulsion results from varying the cations of the soap present. The use of a trialkanolammonium cation based soap has been found to produce a surprisingly stable emulsion.

In the present invention, it is important to form the soap by mixing the fatty acids and the base in the emulsification process, that is, the soap must be formed in-situ. Preformed soap was found not to provide such stable emulsions.

According to a second aspect the present invention consists in a method of preparing a silicone oil-in-water emulsion including;

forming a first mixture including a silicone oil, a base, and initial water;

combining the first mixture with one or more fatty acids having from 8 carbon atoms to 18 carbon atoms;

emulsifying the resultant combination; and wherein a soap is formed in situ in the process of emulsification.

If the one or more fatty acids are a wax or a solid, then preferably it is liquefied prior to combining with the first mixture. Preferably the liquification occurs by heating.

The silicone oil may be present in the oil-in-water emulsion in the broad range of from a few percent by weight or less to around 70%. The amount is not critical, as a skilled addressee may be able to determine this for the purpose of the present invention. Preferably in the case of the shower gel, the silicone oil is added in an amount such that it totals from 30% to 60% w/w of the resultant emulsion. More preferably the silicone oil totals around 50–60% w/w of the resultant emulsion. Preferably the base is added in such an amount that it totals at least 1 mole equivalent with respect to the carboxylic groups of the one or more fatty acids present in the mixture. Preferably, the initial water is added in such an amount that it totals from 3% to 10% w/w of the resultant emulsion. More preferably the initial water totals around 3.3% w/w of the resultant emulsion.

Preferably the emulsification is by mechanical agitation means. The agitation means include, but are not limited to, a homomixer, emulsifier, homogenizer or colloidal mill. More preferably, the emulsification is by high shear means. An example is a trishaft mixer with two high speed disperser shafts and one anchor scraper, known in the art as a "Change Can", "Turello" or "Combi" mixer.

The soap stabilized oil-in-water emulsion can further include addition of additional water. This additional water, for example, dilution water, can be added during emulsification or subsequent to emulsification to provide the desired concentration of effective component. Optionally the mixture can include a biocide.

Preferably if additional water and/or biocide is added, this is done so under vacuum to reduce foaming.

DESCRIPTION OF THE PREFERRED EMBODIMENTS

The first mixture is prepared by mixing the silicone oil, the base and the water, followed by addition of a second mixture of one or more fatty acids having from 8 carbon atoms to 18 carbon atoms. The resultant mixture is mechanically sheared to produce a soap from the base and the fatty acid(s) in situ with concurrent emulsification of the mixture. Additional water may be added during and/or subsequent to the emulsifying process to produce a final stable emulsion.

The addition of initial water is important in terms of achieving the desired particle size. A value for initial water is chosen such that two criteria are satisfied: i) a thick phase emulsion forms and ii) the desired particle size is reached. The first criteria sets the minimum value, as if it is too low there is not enough water to form a continuous water phase and the second criteria sets the maximum value since if too much initial water is present the surfactants are too dilute to achieve particle size reduction. Once the desired particle size is achieved the dilution water (and minors such as biocide) can be added. In general, the steps for forming the submicron soap emulsions of the present invention are:

1. Mix triethanolamine (base), silicone fluid/polymer, and initial water in a Change Can until uniform
2. Add melted fatty acid to form soap under medium shear
3. Increase shear to reduce particle size Once the desired particle size is achieved, any dilution water and minor ingredients are added under vacuum to prevent aeration.

The stable silicone oil-in-water emulsion of the present invention is accomplished by forming the soaps in situ by adding the fatty acid(s) and the base individually, thereby achieving the emulsion of very small particle sizes.

While any silicone oil is suitable for use in the present invention, polydiorganosiloxanes are generally preferred. The most suitable poly siloxanes are discussed above.

A blend of long chain fatty acids, wherein the carbon backbone varies from $C_8$ to $C_{18}$, has been found to produce a more stable emulsion than a single long chain fatty acid or a synthetic surfactant.

An explanation as to why a blend of fatty acids have better stability than single chain length soaps is given below, although it is to be understood that such an explanation in no way limits the scope of the monopoly sought. Soaps obtained from different fatty acids will position themselves differently at the particle water interface. Varying the length of the fatty acid chain will cause changes to the acidity and the hydrophobicity of the soap molecule, which in turn is thought to vary the way different soap molecules provide particle stabilization.

While the mechanism of vesicle formation (ie. a droplet of silicone oil with fatty acids surrounding it, charge outwards) has not been thoroughly investigated, it will be appreciated that the nature of such a vesicle will be different if a mixture of different fatty acids is used rather than a single compound where all the molecules are of the same length.

Surprisingly, it has also been found that a significant and hitherto unexpected difference in the stability of the emulsion results from varying the cations present. Soaps can be formed from many different cations, for example, $K^+$, $Na^+$ or protonated amines such as triethanolamine, aminomethylpropanol etc. The triethanolammonium cation has been found to produce very stable emulsions when used in the present invention. This has been observed to be the case both for the silicone oil-in-water emulsions per se and also when these are incorporated into complete shower gel products.

It is postulated that the larger size of this cation and the shielding of the charge on the central nitrogen atom by the ethanol chains results in an emulsion where there is far less mobility of charge.

It is also possible that such mixtures of fatty acids alone or in conjunction with the use of a triethanolamine may have application in other areas of personal care, such as more traditional solid soap bars, or in unrelated industries such as the textile and plastics industries.

EXAMPLES

In the following examples, Fatty Acid Blends A and B and Soap Shower Gel base formulation are defined as follows:

| Fatty Acid Blend A | |
|---|---|
| Lauric ($C_{12}$) acid | 57 wt. % |
| Myristic ($C_{14}$) acid | 35 wt. % |
| Stearic ($C_{18}$) acid | 8 wt. % |
| Fatty Acid Blend B* | |
| Capric acid ($C_{10}$ saturated) | 2 wt. % |
| Lauric acid ($C_{12}$ saturated) | 55 wt. % |
| Myristic acid ($C_{14}$ saturated) | 21 wt. % |
| Palmitic acid ($C_{16}$ saturated) | 10 wt. % |
| Stearic acid ($C_{18}$ saturated) | 12 wt. % |
| Oleic acid ($C_{18:1}$ unsaturated) | <0.5 wt. % |

*Fatty acids blend B is commercially available as stripped, cracked and hardened coconut oil from Henkel Co.

| Soap Shower Gel Base | |
|---|---|
| Lauric Acid | 15.4% |
| Myristic Acid | 9.5% |
| Stearic Acid | 2.2% |
| KOH (50% solution) | 14.2% |
| Water (purified) | 47.0% |
| Glycerin | 4.0% |
| Propylene Glycol | 4.0% |
| Preservative | 0.5% |
| Pearliser | 2.2% |
| Thickener | 0.5% |
| Buffers | 0.3% |
| Perfume | trace |

Part means part by weight, and the viscosity is one measured at 25° C., unless otherwise described.

Example 1

In a Change Can mixer bowl, 2.8 parts of triethanolamine was blended with 60.0 parts of polydimethylsiloxane oil having the viscosity of 0.06 m²/s (60,000 cs.) and 3.6 parts of initial water with the dispersers on 1,200 rpm (4.5 m/sec tip speed) and scraper on 30 rpm. After 10 minutes the disperser speed was increased to 3,000 rpm (11.0 m/sec) and 4 parts of melted Fatty Acids Blend B was slowly and steadily added. Increasing the disperser speed up to 5,000 rpm (19 m/sec) the mixture was sheared for 22 minutes until the desired particle size was achieved. After stopping the dispersers, 29.4 parts of dilution water was added to the mixture with 0.2 parts of biocide, and the vessel was sealed and subject to vacuum until 80 kPa was reached. Afterwards the dispersers were run at 2,000 rpm until the mixture was uniform.

The oil-in-water emulsion containing 60.0 wt. % of silicone oil was obtained and found to have the particle sizes, d(50%) of 0.3 2 micrometers and d(90%) of 0.6 micrometers. It was found to be stable for 12 months at ambient conditions; greater than 4 months at 40° C.; greater than 6 weeks at 50° C., and was also stable for more than 10 freeze thaw cycles.

Example 2

Using the same mixer as Example 1, 60.0 parts of hydroxy end capped polydimethylsiloxane having a viscosity of 0.1 m²/s (100,000 cs.), 2.8 parts of triethanolamine and 3.0 parts of initial water were blended with dispersers on 600 rpm and scraper on 30 rpm. After cooling, 4.0 parts of melted Fatty Acids Blend B were added while the shear was increased to 1,200 rpm on the dispersers. Further water was added in an amount of 3.2 parts to establish a thick phase. The shear was increased to 5,000 rpm on the dispersers for 40 minutes. 26.8 parts of dilution water and 0.2 part of biocide were added and mixed under vacuum with the dispersers on 1,200 rpm.

An oil-in-water emulsion containing 60.0 wt. % of silicone oil was obtained with the particle sizes, d(50%) of 0.32 micrometers and d(90%) of 0.6 micrometers.

This emulsion in an amount of 5.0% per the total was added to Soap Shower Gel base and found to have good stability with up to 9 months at room temperature showing no signs of stratification of separation.

Example 3

60.0 parts of trimethylsilyl end capped polymethylphenylsiloxane containing about 11 mole % of phenylmethyl siloxane units and having a viscosity of $50 \times 10^{-6}$ m$^2$/s (50 cs.), 2.8 parts of triethanolamine and 3.3 parts of water were added to a Sardik mixer (that has one high speed disperser which runs central to the bowl, and the bowl counter rotates with respect to the shaft) and blended together. 4 parts of melted Fatty Acids Blend B was added as the shear was increased. A further 8.1 parts of water was added to the batch to enable a thick phase to form. 21.6 parts of dilution water and 0.2 part of biocide were admixed thereto under vacuum. The oil-in-water emulsion containing 60.0% of methyl phenyl silicone oil was produced having particle sizes, d(50%) of 0.51 micrometers and d(90%) of 0.9 micrometers. This emulsion showed the same stability as Example 1.

Example 4

Example 1 was repeated to produce the silicone emulsion which had the formulation as follows:

| | |
|---|---|
| Silicone oil (as used in Example 1) | 12.3 parts |
| Water | 81.5 parts |
| Potassium soap | 6.0 parts |
| (formed from lauric acid and KOH) | |
| Thickener (Xanthan Gum) | 0.5 parts |

This silicone emulsion was stable for one month, but when the silicone emulsion was mixed with Soap Shower Gel base, stratification happened in about three days.

Example 5

Example 1 was again repeated to produce the silicone emulsion which had the formulation as follows:

| | |
|---|---|
| Silicone oil (same as used in Example 1) | 53.0 parts |
| Oleic acid* | 5.3 parts |
| Potassium hydroxide solution | 1.2 parts |
| Water | |
| Initial | 16.0 parts |
| Additional | 23.7 parts |
| Thickener (Xanthan Gum) | 0.1 parts |
| Preservative | 0.2 parts |
| Anti-oxidant (Vitamin E derivative) | 0.5 parts |

*Oleic acid employed herein consisted of 74% oleic acid, 11% palmitoleic acid, 4% linoleic acid, 3% myristoleic acid and 8% saturated acid.

This silicone emulsion was also stable for one month, but when the silicone emulsion was added to Soap Shower Gel base, it became unstable within 5 days at room temperature.

Example 6

Using the same mixer as in Example 1, 11.8 parts of hydroxy end capped polydimethylsiloxane gum having a viscosity of 70m$^2$/s (70,000,000 cs.) and 48.2 parts of trimethylsilyl end capped polydimethylsiloxane were blended with dispersers on 1,000 rpm and scraper on 30 rpm for 6 hours. To the blend, 2.8 parts of triethanolamine and 6.3 parts of initial water were admixed with dispersers on 1,000 rpm and scraper on 40 rpm. Afterwards, 4.0 parts of melted Fatty Acid Blend B were added while the shear was increased to 5,000 rpm on the dispersers for 50 minutes total. 26.8 parts of dilution water and 0.2 part of biocide were added and mixed under vacuum.

The oil-in-water emulsion containing 60.0 wt. % of silicone component was obtained with the particle sizes, d(50%) of 0.33 micrometers and d(90%) of 0.58 micrometers. This emulsion was stable, using centrifuge testing, dilution testing, freeze-thaw test (10 cycles) and no creaming was found on storage after 9 months at room temperature.

Example 7

50.0 parts of carboxy functional trimethylsilyl end capped polydimethylsiloxane containing two mole % of carboxy functional groups bonded to the silicon atom via propylene groups and having a viscosity of $2,500 \times 10^{-5}$ m$^2$/s (2,500 cs.), 2.8 parts of triethanolamine and 10.0 parts of water were added to a Sardik mixer of Example 3 and blended together. 4 parts of melted Fatty Acid Blend B was added while the shear was increased. A further 2.3 parts of water was added to the batch and sheared for another 3 minutes. 30.7 parts of dilution water and 0.2 part of biocide were admixed thereto under vacuum. The oil-in-water emulsion containing 50.5% of the silicone oil was produced to have the particle sizes, d(50%) of 0.31 micrometers and d(90%) of 0.053 micrometers. This emulsion showed stability for up to 3 months at room temperature.

COMPARATIVE EXAMPLES

Comparative Example 1

Polydimethylsiloxane oil (PDMS) having a viscosity of 0.06 m$^2$/s (60,000 cs.) (PDMS) and potassium soaps of the above Fatty Acids Blend A (K-Soap) were added to water as shown in the Table below in the Sardik bowl to form mixtures No. 1, No. 2 and No. 3. No. 1 mixture was sheared for 25 minutes. Nos. 2 and 3 mixtures were sheared for 15 minutes to obtain emulsions respectively. 0.2 parts of Biocide was added to the emulsion in the same manner as described in Example 1. The emulsions had solid contents of 56.4%, 58.5% and 60.3% respectively.

| | PDMS | K-Soap | Water | Biocide |
|---|---|---|---|---|
| No. 1 (30% solid Soap) | 53.0 parts | 10.7 parts | 36.1 parts | 0.2 parts |
| No. 2 (40% solid Soap) | 55.3 parts | 7.5 parts | 37.0 parts | 0.2 parts |
| No. 3 (53% solid Soap) | 57.1 parts | 5.7 parts | 37.0 parts | 0.2 parts |

The K-Soap (30% solid) was previously prepared from 13 parts of KOH (50% solid) and 25 parts of the Fatty Acids Blend A.

The particle size of No. 1 emulsion reached to d(50%) of 1.67 micrometers, but the stage water (soap past dilution water) was too high to further reduce the particle size. No. 2 emulsion and No. 3 emulsion had the particle sizes, d(50%) of 1.06 micrometers and 0.77 micrometers respectively.

These comparative examples showed that the use of K-Soap paste in the emulsification made particle size control/reduction very difficult and once the K-Soap paste was above 40% solids, it became very difficult to work with due to high viscosity and-gelling.

Comparative Example 2

53 Parts of polydimethylsiloxane oil having the viscosity of 0.06 m$^2$/s (60,000 cs.) and 6 parts of potassium soap of oleic acid were added to 40 parts of water in the Sardik bowl to form the mixtures. The mixture was sheared for 25 minutes. Nos. 2 and 3 mixtures were sheared for 15 minutes to obtain an emulsion with 59% solid excluding biocide. 0.2 parts of Biocide was added to the emulsion in the same manner as described in Example 1.

This emulsion obtained was mixed with the Soap Shower Gel base above but the product failed to show the stability for the 12 months shelf life.

Comparative Example 3

17.6 parts of triethanolamine was mixed with 60 parts of water and heated to 70° C. With continuous stirring, 25 parts of melted Fatty Acids Blend A was added thereto. After the heating was stopped, the stirring was continued for 20 minutes to cool the soap obtained. The soap (40% solid) was highly viscous like gel, which could not be easily worked with.

7.5 parts of the above soap and 57.3% of polydimethylsiloxane oil having the viscosity of 0.06 m$^2$/s (60,000 cs.) were added to 35 parts of water in the Sardik bowl and sheared for 9 minutes to produce an emulsion. 0.2 parts of Biocide was added to the emulsion in the same manner as described in Example 1. The solid content of the emulsion was 61.5%.

What is claimed is:

1. A method of forming a soap stabilized oil-in-water emulsion including the steps of emulsifying a silicone oil in water in the presence of soap; said soap including a cation derived from a base and a carboxylate anion derived from one or more fatty acids having from 8 to 18 carbon atoms; and wherein the soap is formed in situ by reacting the base and the fatty acid(s) in progress of the emulsification wherein additional water is added under vacuum to reduce foaming.

2. A method of forming a soap stabilized oil-in-water emulsion including the steps of:

forming a first mixture comprising a silicone oil, a base, and initial water;

combining the first mixture with one or more fatty acids having from 8 carbon atoms to 18 carbon atoms;

emulsifying the resultant combination; and wherein a soap is formed in situ in the process of emulsification, and additional water is added under vacuum to reduce foaming.

3. A method of forming a soap stabilized oil-in-water emulsion according to claim 1, wherein the emulsification is by mechanical agitation means.

4. A method of forming a soap stabilized oil-in-water emulsion according to claim 1 wherein the emulsification is by high shear means.

5. A method according to claim 1 wherein the additional water is added during emulsification.

6. A method according to claim 1 wherein the additional water is added subsequent to emulsification.

7. A method according to claim 1 further including the step of adding a biocide.

* * * * *